(12) United States Patent
Shibuya et al.

(10) Patent No.: US 9,981,205 B2
(45) Date of Patent: May 29, 2018

(54) PURIFICATION DEVICE, AND PURIFICATION METHOD

(71) Applicant: HITACHI, LTD., Tokyo (JP)

(72) Inventors: Keisuke Shibuya, Tokyo (JP); Yui Sugita, Tokyo (JP); Ryouichi Haga, Tokyo (JP); Masaru Nanba, Tokyo (JP)

(73) Assignee: HITACHI, LTD., Tokyo (JP)

( * ) Notice: Subject to any disclaimer, the term of this patent is extended or adjusted under 35 U.S.C. 154(b) by 367 days.

(21) Appl. No.: 14/787,428

(22) PCT Filed: May 7, 2014

(86) PCT No.: PCT/JP2014/062249
§ 371 (c)(1),
(2) Date: Oct. 27, 2015

(87) PCT Pub. No.: WO2014/181796
PCT Pub. Date: Nov. 13, 2014

(65) Prior Publication Data
US 2016/0144294 A1    May 26, 2016

(30) Foreign Application Priority Data

May 7, 2013   (JP) .................................. 2013-097596

(51) Int. Cl.
*B01D 15/38* (2006.01)
*B01J 20/24* (2006.01)
(Continued)

(52) U.S. Cl.
CPC ..... *B01D 15/3809* (2013.01); *B01D 15/3876* (2013.01); *B01J 20/24* (2013.01);
(Continued)

(58) Field of Classification Search
CPC .. B01D 15/3809; B01D 15/3876; B01J 20/24; B01J 20/286; B01J 20/3272;
(Continued)

(56) References Cited

U.S. PATENT DOCUMENTS

2004/0039177 A1    2/2004   Yamanaka et al.
2004/0134846 A1    7/2004   Akiyama et al.
(Continued)

FOREIGN PATENT DOCUMENTS

EP        1 960 428 B1    7/2011
EP        2657254 A1      10/2013
(Continued)

OTHER PUBLICATIONS

JP 2012-146610 Priority Application to U.S. 2015/0191506 (Filed Jun. 29, 2012).*

(Continued)

*Primary Examiner* — Lucas Stelling
(74) *Attorney, Agent, or Firm* — Oliff PLC

(57) ABSTRACT

Provided is a purification device for purifying a useful substance (i.e., target substance) without using an acidic eluent. The purification device purifying the target substance comprises a column and a filler packed in the column. The filler contains a carrier, a temperature responsive polyamino acid bonded to the carrier, and a binding substance bonded to the temperature responsive polyamino acid and specifically bonding to the target substance.

21 Claims, 5 Drawing Sheets

(51) Int. Cl.
*B01J 20/286* (2006.01)
*B01J 20/32* (2006.01)
*B01J 20/34* (2006.01)
*C07K 1/22* (2006.01)

(52) U.S. Cl.
CPC ......... *B01J 20/286* (2013.01); *B01J 20/3272* (2013.01); *B01J 20/3425* (2013.01); *B01J 20/3475* (2013.01); *B01J 20/3483* (2013.01); *C07K 1/22* (2013.01); *B01J 2220/58* (2013.01)

(58) Field of Classification Search
CPC ............... B01J 20/3425; B01J 20/3475; B01J 20/3483; B01J 2220/58; C07K 1/22
See application file for complete search history.

(56) References Cited

U.S. PATENT DOCUMENTS

| | | |
|---|---|---|
| 2010/0190965 A1 | 7/2010 | Yamaguchi et al. |
| 2015/0191506 A1* | 7/2015 | Okuyama .......... B01D 15/3809 525/54.1 |

FOREIGN PATENT DOCUMENTS

| | | |
|---|---|---|
| JP | 2002-119854 A | 4/2002 |
| JP | 2007-230871 A | 9/2007 |
| JP | 2009-520691 A | 5/2009 |
| WO | 01/074482 A1 | 10/2001 |
| WO | 08/156124 A1 | 12/2008 |
| WO | 2012/086837 A1 | 6/2012 |
| WO | 2012/165356 A1 | 12/2012 |

OTHER PUBLICATIONS

English Language Translation of JP 2012-146610 Priority Application to U.S. 2015/0191506 (Filed Jun. 29, 2012).*

Malmstadt et al. "A Smart Microfluidic Affinity Chromatography Matrix Composed of Poly (N-isopropylamide)-Coated Beads," Anal. Chem. 2003, 75, 2943-2949.

Jan. 2, 2017 Extended Search Report issued in European Patent Application No. 14794907.7.

Aug. 19, 2014 Search Report issued in International Patent Application No. PCT/JP2014/062249.

Tachibana, Yoichi et al., "Biodegradable thermoresponsive poly(amino acid)s", Chemical Communications, 2003, No. 1, Jan. 7, 2003, pp. 106-107.

* cited by examiner

POLY(N-SUBSTITUTED α/β ASPARGINE)

AMPHIPATHIC POLYAMINO ACID

FIG.3

TEMPERATURE RESPONSIVE POLYAMINO ACID
PTOTEIN A
TARGET SUBSTANCE
HYDROPHYLIC GRAOUP
CARRIER
HYDROPHOBIC GROUP
STRUCTURAL CHANGE
CARRIER

≤20°C    37°C

PURIFICATION DEVICE, AND PURIFICATION METHOD

TECHNICAL FIELD

The present invention relates to a purification device and a purification method.

BACKGROUND ART

Useful substances produced by cultivation are utilized in various fields. Such useful substances, for example, include a therapeutic antibody. That therapeutic antibody is obtained by cultivating animal cells and purifying a culture solution of the animal cells.

When animal cells are cultivated, useful substances are secreted extracellularly. Consequently, after removing the animal cells, those useful substances are purified via chromatography. On the other hand, when microorganisms are cultivated, useful substances are secreted intracellularly. In this case, after disrupting the cells and removing solid materials, those useful substances are purified via chromatography.

Generally, a therapeutic antibody, which is an example of useful substances, is purified by using a plurality of types of chromatography through a rough purification step, an intermediate purification step, and a final purification step. Herein, affinity chromatography is used in the rough purification step, and hydrophobic chromatography and ion exchange chromatography or the like are used in the intermediate and final purification steps.

Here, the related art of this technical field is disclosed by Patent Literatures 1-4.

CITATION LIST

Patent Literatures

Patent Literature 1: International Publication No. WO01/074482 Pamphlet
Patent Literature 2: Japanese Unexamined Patent Application Publication No. 2002-119854
Patent Literature 3: International Publication No. WO08/156124 Pamphlet
Patent Literature 4: Japanese Unexamined Patent Application Publication (Translation of PCT Application) No. 2009-520691

SUMMARY OF INVENTION

Technical Problem

When a useful substance is purified by using affinity chromatography disclosed in Patent Literatures 1-4, the useful substance is eluted by using an acidic eluent. However, use of an acidic eluent may cause aggregation of the useful substance or decrease in activity, leading to deterioration in the quality thereof.

Solution to Problem

Therefore, an object of the present invention is to provide a purification device and a purification method by which a useful substance is purified without using an acidic eluent.

Means for Solving Problem

Earnest examination of the present inventors has resulted in finding of a column packed with a filler containing a carrier, a thermoresponsive polyamino acid bonded to the carrier, and a biding substance bonded to the thermoresponsive polyamino acid and specifically bonding to a useful substance (i.e., target substance). Accordingly, the present inventors have found that the above column enables a target substance to be purified via controlling a temperature of the column without using an acidic eluent.

Advantageous Effect

According to the present invention, a target substance is purified by chromatography without using an acidic eluent.

BRIEF DESCRIPTION OF DRAWINGS

FIG. 1 shows a purification device in a preferable embodiment of the present invention.
FIG. 2 shows an example of a temperature responsible polyamino acid.
FIG. 3 shows a structural change of a temperature responsive polyamino acid.

EMBODIMENTS FOR CARRYING OUT PRESENT INVENTION

Figure 4:
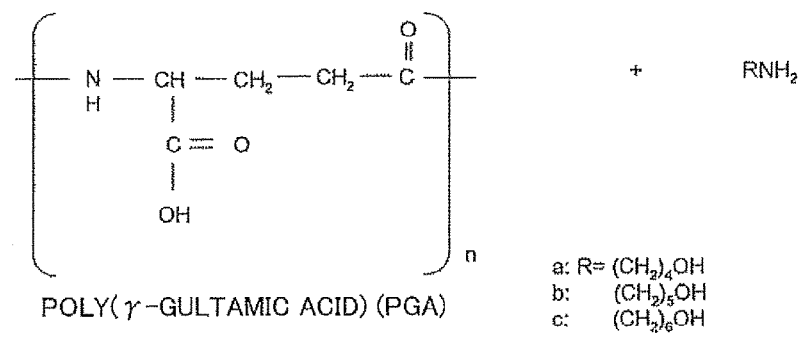
FIG. 4 shows an example of synthesizing a temperature responsive polyglutamic acid.

Hereinafter, the present invention will be described in more detail.

<Purification Device>

The present invention relates to a purification device including a column packed with a filler containing a carrier, a temperature responsible polyamino acid bonded to the carrier, a binding substance bonded to the temperature responsive substance and specifically bonding to a target substance.

Here, the carrier is not specifically limited as long as the carrier bonds to a temperature responsive polyamino acid. For example, a carrier packed in a column of general affinity chromatography may be used. A surface of the carrier may be chemically treated to make a bond formation with a temperature responsive polyamino acid.

The temperature responsive polyamino acid may change the conformation thereof as the temperature changes. The resulting change in conformation of the temperature responsive polyamino acid caused by the change in temperature effects a bond formation between the binding substance and the target substance. As a result, this effect may make the target substance bond to and separate from the binding substance.

As shown in FIG. 3, for example, the temperature responsive polyamino acid has a conformation making the target substance bond to the binding substance (e.g., Protein A) at 20° C. or less. On the contrary, the temperature responsive polyamino acid has a conformation making the target substance bonded to the binding substance separate therefrom at 37° C.

In the present invention, a conformational change of the temperature responsive polyamino acid caused as the temperature changes is used for column purification. Therefore, it is unnecessary to use an acidic eluent therefor. This feature enables purification of the target substance to be conducted under neutral PH conditions, thereby to avoid aggregation of the target substance and decrease in the activity thereof. Accordingly, the quality and productivity of the target substance may be improved. Further, the reversible profile of the conformational change allows the temperature responsive polyamino acid to be reused.

Note that a conformational change of the temperature responsive polyamino acid is observed as a phase transition. Such a phase transition includes, for example, a sol-gel transition.

Here, preferably, a conformational change of the temperature responsive polyamino acid may occur, for example, in the range from 0 to 60° C., more preferably in the range from 4 to 40° C. This temperature range may suppress deterioration of the target substance. Further, this temperature range may avoid freezing of a buffer solution used for eluting the target substance, and precipitation of salts in the buffer solution.

The temperature responsive polyamino acid includes, for example, polylysine, polyglutamic acid, polyasparagine or the like. A side chain may be introduced on those polyamino acids.

Further, modification of a molecular weight and a side chain of the polyamino acid may appropriately control a critical solution temperature causing the conformational change of the temperature responsive polyamino.

A preferable molecular weight of the temperature responsive polyamino acid varies depending on a type of the polyamino acid. However, preferably the molecular weight is, for example, 1-20 kDa, more preferably 2-18 kDa, most preferably 3-16 kDa.

A side chain of the temperature responsive polyamino acid includes, for example, an amphipathic group, a hydrophobic group, and a hydrophilic group. More specifically, preferably the temperature responsive polyamino acid may include an amphipathic group in a side chain. Further, preferably the temperature responsive polyamino acid may include both hydrophobic group and hydrophilic group in side chains.

An amphipathic group includes, for example, a carboxyl butylamino group, a carboxyl propylamino group or the like. A hydrophobic group includes, for example, an alkylamino group, specifically, a dodecylamino group or the like. A hydrophilic group includes, for example, a hydroxy alkylamino group, specifically, a 3-hydroxy propylamino group or the like.

Further, a temperature responsive polyamino acid having a side chain includes, for example, polyasparagine containing a monomer unit with a dodecylamino side chain and a monomer unit with a hydroxy alkylamino side chain, as shown in FIG. 2. Note that in FIG. 2, "n" represents a polymerization degree of the polyasparagine and "x" represents the number of carbon atoms in the alkylene group.

Figure 5:
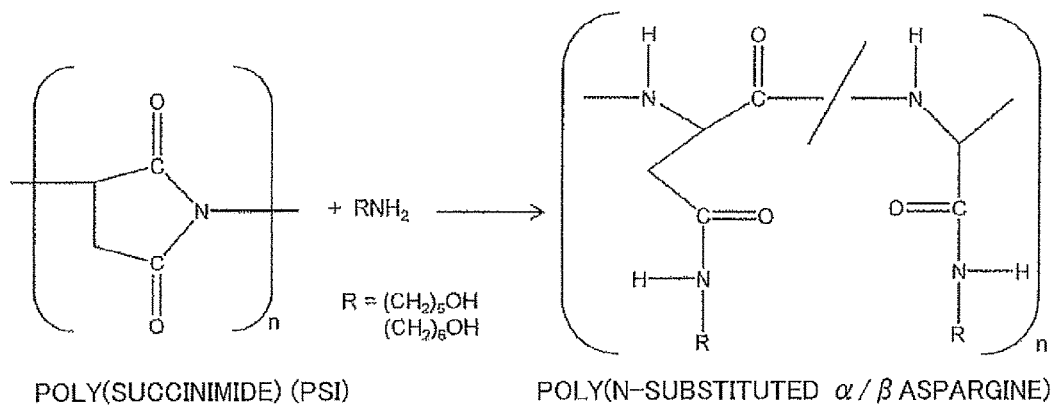
FIG. 5 shows an example of synthesizing a temperature responsive polyasparagine.

Polyasparagine having a side chain is synthesized, for example, by introducing an amino alcohol etc. into the polysuccinimide as shown in FIG. 5. Similarly, polyglutamic acid having a side chain is synthesized, for example, by introducing a hydroxy alkylamino group etc. into the poly-glutamic acid as shown in FIG. 4. Note that "n" in FIGS. 4 and 5 represents a polymerization degree of the poly($\gamma$-glutamic acid).

A bond between a temperature responsive polyamino acid and a carrier should have bonding strength so that the temperature responsive polyamino acid does not separate from the carrier under the purification conditions of a target substance. Such a bond includes, for example, a covalent bond, more specifically, an amide bond and an ester bond or the like.

A binding substance is not particularly limited as long as the binding substance has ability for specifically bonding to a specific target substance. Hereby, a binding substance may be appropriately selected or prepared depending on a type of the target substance. Although such a binding substance is not particularly limited, a protein, more specifically, Protein A may be preferably used as a binding substrate.

A bond between a binding substrate and a temperature responsive polyamino acid should have bonding strength so that the binding substrate does not separate from the temperature responsive polyamino acid under the purification conditions of a target substance. Such a bond includes, for example, a covalent bond, more specifically, an amide bond and an ester bond or the like.

Further, a target substance is not particularly limited. For example, the target substance is preferably a low molecular compound or a high molecular compound having a biological activity, more preferably a protein such as an antibody or an enzyme, most preferably an antibody usable as a medicine. Such a target substance may be produced by cultivation of animal cells, plant cells, insect cells, yeast, bacteria, fungi, or algae or the like.

A bond between a target substance and a binding substance should have bonding strength so that the target substrate separates from the binding substance by the conformational change of the temperature responsive polyamino acid. Such a bond includes substance-substance interactions, for example, ionic affinity, adsorptive affinity or hydrophobic affinity.

In an embodiment of the present invention, a purification device may further include a temperature controller that changes a temperature of the temperature responsive polyamino acid in the range, for example, from 0 to 60° C., preferably 4 to 40° C. The temperature controller allows the conformational change of the temperature responsive polyamino acid, realizing a bond formation of the target substance with the binding substance, and separation of the target substance from the temperature responsive polyamino acid. Further, the temperature controller may control the temperature without deteriorating the target substance. Such a temperature controller includes, for example, a heater heating a tank in which an eluent is stored or a column heater heating a column.

In an embodiment of the present invention, the purification device further includes a tool which further purifies a target substance thus purified by the column. Such a tool includes, for example, an anion exchange column packed with anion exchange resin, or a cation exchange column packed with cation exchange resin. According to the present invention, unnecessity of an acidic eluent may prevent an acidic eluent from damaging an ion exchange column.

In an embodiment of the present invention, the purification device may further include a virus inactivation/removal unit for a target substance thus purified by the column. Such a virus inactivation/removal unit includes, for example, an ultrafiltration (UF) apparatus, nanofiltration (NF) apparatus, a liquid heat treatment apparatus, or a solvent/detergent (S/D) treatment apparatus. A conventional purification device may include one virus inactivation/removal unit since use of an acidic eluent inactivates viruses. On the contrary, according to the present invention, viruses are not inactivated since a neutral eluent is used therein. Thereby, preferably the purification device of the present invention may include at least two virus inactivation/removal units.

Here, FIG. 1 shows a preferable embodiment of the purification device according to the present invention. In FIG. 1, an ion exchange column 3, a cation exchange column 4, an ultrafiltration (UF) apparatus 5, and a disinfection filter 8 are arranged in that order at the downstream of an affinity column 2. A column including a temperature responsive polyamino acid and a binding substance of the present invention is used as the affinity column 2. At the upstream of the affinity column 2, a media reservoir 1, a cooling apparatus 7 and an eluent tank 6 are arranged. Note that the cooling apparatus 7 cools the culture liquid at 20° C. or less, which is obtained via culturing at a predetermined temperature (e.g., 37° C.) in a culture step. The cooling process is performed by circulating water. However, the cooling process is not limited to water circulation.

Further, as shown in FIG. 1, fraction tanks 9 and reservoirs 10 are optionally arranged where necessary. Herein, each of the fraction tanks 9 stores each component obtained via fractionating a plurality of components contained in a solution treated by each column. Each of the reservoirs 10 receives and stores a solution.

<Purification Method>

The present invention also relates to a purification method of a target substance, including a binding step, a cleaning step, a separation step and an eluting step.

The biding step is conducted by passing a solution containing a target substance and impurities through a column packed with a filler that contains a carrier, a temperature responsive polyamino acid bonded to the carrier, and a binding substance bonded to the temperature responsive polyamino acid and specifically bonding to the target substance. As a result, in the binding step, the target substance is made bonded to the binding substance.

Hereinbefore, the carrier, the temperature responsive polyamino acid, the binding substance and the target substance have been described. The solution containing the target substance and impurities may be, for example, a culture liquid obtained via cultivation of animal cells, plant cells, insect cells, yeast, bacteria, fungi, and algae or the like.

A temperature in the binding step may be set so that the temperature responsive polyamino acid takes a conformation capable of making the target substance bonded to the binding substance. For example, the binding step may be conducted at 0-60° C., preferably at 2-20° C., more preferably 4-10° C. A pH value in the binding step is set at 5-9, preferably at 6-8. The binding step performed under those conditions enables the target substrate to be made bonded to the binding substrate without deteriorating the target substrate.

The cleaning step is conducted by washing out the impurities without separating the target substance bonded to the binding substance so as to clean the inside of the column. A solvent used in the cleaning step is not particularly limited as long as the solvent does not damage the binding between the binding substance and the target substance. Preferably, a temperature and a pH value in the cleaning step are set the same as in the binding step. A solvent used in the cleaning step may be selected from, for example, a sodium phosphate solution (20 mM, pH=7.5) or an ammonium sulfate solution (0.8 M, pH=7.5) or the like.

The separation step is conducted by changing the temperature of the temperature responsive polyamino acid so as to make the target substance separate from the binding substance. A temperature in the separation step may be set so that the temperature responsive polyamino acid takes a conformation that makes the target substance bonded to the binding substance separate therefrom. For example, the separation step may be conducted at 0-60° C., preferably at 20-50° C., most preferably at 35-40° C. Further, a pH value in the separation step may be set, for example, at 5-9, preferably at 6-8. The separation step performed under those conditions may make the target substance separate from the binding substance without deteriorating the target substance.

The eluting step is conducted by eluting the separated target substance. A solvent used for eluting the target substance may be the same as in the cleaning step, or different from the solvent in the cleaning step. Preferably, a temperature and a pH value in the eluting step are the same as in the separation step.

In an embodiment of the present invention, the purification method may further include an additional purification step of further purifying the target substance thus eluted in the eluting step by using an anion exchange column and/or a cation exchange column.

In an embodiment of the present invention, the purification method may further include a virus inactivation/removal step of conducting a virus inactivation/removal treatment for the target substance thus eluted in the eluting step or the target substance further purified by the ion exchange column. Preferably, the virus inactivation/removal step may be conducted two times. The virus inactivation/removal step may be performed by a virus inactivation/removal unit previously explained hereinbefore.

<Preparation of Temperature Responsive Polylysine>

Temperature responsive polylysine may be prepared by the following procedure.

Water soluble carbodiimide (WSC) (290 mg), N-hydroxysuccinimide (NHS) (170 mg), and valeric acid (130 µl) were dissolved in distilled water or a phosphate buffer solution (PBS) (pH=5.8) (4 ml) put in a glass vessel. The resultant solution was cooled at 4° C., and polylysine (140 mg) was added therein. The mixture was stirred overnight (or for 2 hr at 37° C.). Then, the reaction mixture was purified by a dialysis membrane (cut-off molecular weight=2000, Spectra/Por®) under the condition of being stirred in pure water at room temperature for 24 hr to remove unreacted materials. As a result, temperature responsive polylysine was purified and isolated.

<Preparation of Temperature Responsive Polyaspargine>

Temperature responsive polyasparagine may be prepared by the following procedure.

Into a separable flask (equipped with stirrer, thermometer), was put N,N-dimethylformamide (DMF) (34 g), and polysuccinimide (PSI) (9.7 g, 0.1 mol) was dissolved in DMF. Then, in the resulting solution, were added dodecylamine (6.5 g, 0.035 mol) and 2-methoxyethylamine (4.9 g, 0.065 mol), and the reaction mixture was stirred at 70° C. for 6 hr. The reaction mixture was poured into a large volume of acetonitrile, and resulting precipitate was collected by filtration. The collected precipitate was dried at 60° C. for 24 hr to give temperature responsive polyasparagine (19.4 g, 92% yield).

<Bond Formation Between Binding Substance and Temperature Responsive Polyamino Acid>

Bond formation between the binding substance and the temperature responsive polyamino acid may be performed as the following procedure.

Figure 6:
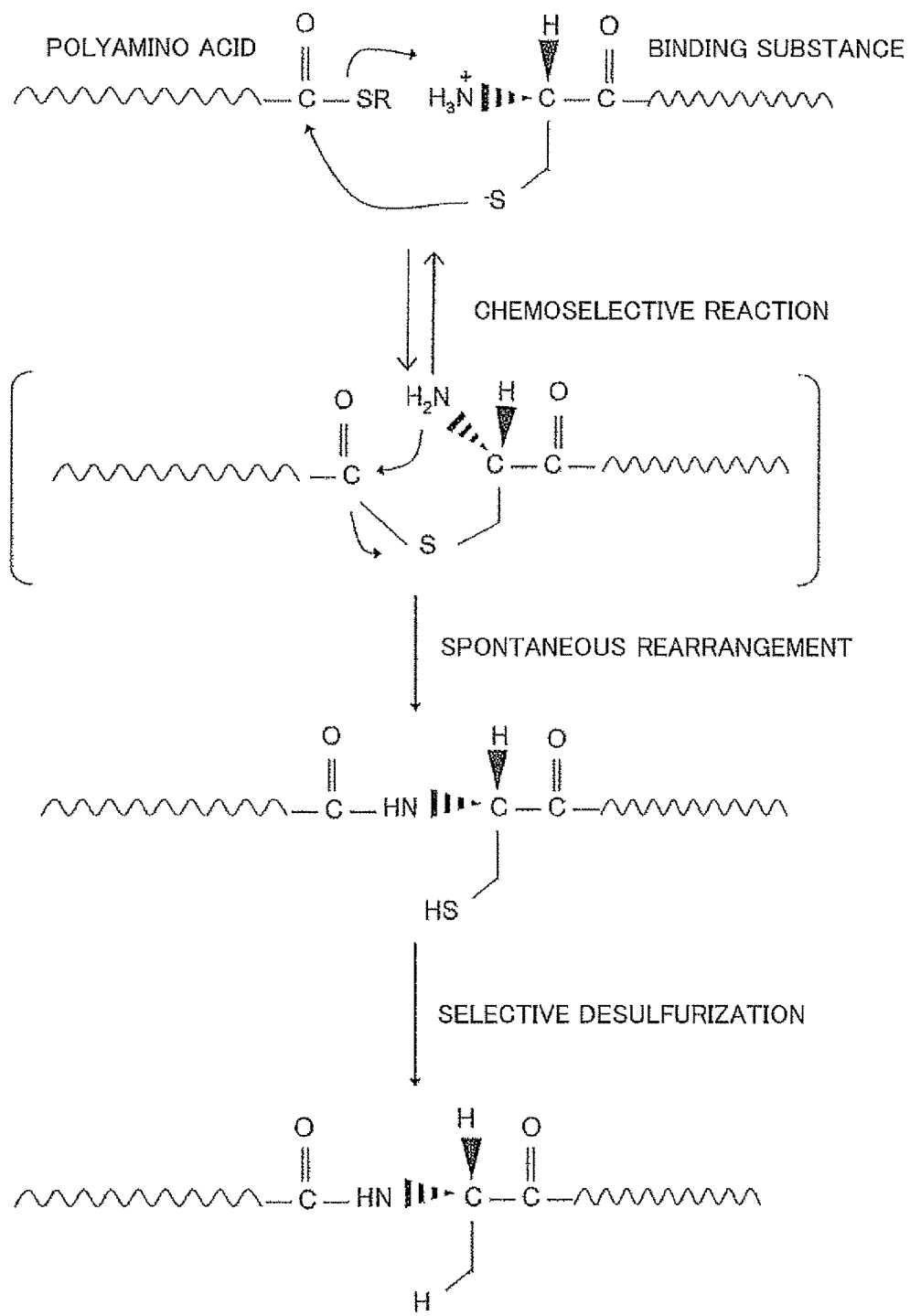
FIG. 6 shows a binding reaction between a binding substance (N-terminal: Cys) and a polyamino acid (C-terminal:thiol).

If the N-terminal of the binding substance is cysteine (Cys), addition of a thiol group to the C-terminal of the polyamino acid enables the binding substance to be bonded to the polyamino acid (Refer to FIG. 6. Note "R" in FIG. 6 is, for example, H). More specifically, the reaction between the C-terminal thioester of the polyamino acid and the N-terminal cysteine of the binding substance makes the two substances bonded each other. The thiol group in the cysteine side chain selectively reacts with the carbonyl carbon of the thioester group (i.e., chemoselective reaction), and via a thiol exchange reaction, a thioester linked initial intermediate is produced. That intermediate spontaneously causes intramolecular rearrangement (i.e., spontaneous rearrangement) to form a natural amide bond at the linkage part, and simultaneously to regenerate a thiol in the cysteine side chain. After the bond formation, the thiol group of the product thus obtained is selectively desulfurized by Raney nickel (i.e., selective desulfurization) to give a natural target sequence. (In other words, the binding substance may be bonded to the temperature responsive polyamino acid.)

Hereinafter, more detailed procedure will be described specifically.

[Preparation of Reagents]

(1) Stock Solution (50 ml):

(a) 0.1 M $Na_2HPO_4$ (disodium hydrogen phosphate) or $NaH_2PO_4$ (sodium dihydrogen phosphate) (1.42 g, 10 mmol)

(b) 6M GuHCl (guanidine hydrochloride) (28.7 g, 300 mmol)

The reagents (a) and (b) are dissolved in a solvent (i.e., water) in that order. The resultant stock solution can be stored at 4.0 for several months. Here, GuHCl is used for solubilizing the peptide reactant. $Na_2HPO_4$ or $NaH_2PO_4$ is used for neutralizing the stock solution at pH 6.8-7.

(2) NCL Buffer:

The following solutes are put in a scintillation vial, and the stock solution (5 ml) thus filtrated (e.g., 0.2 μm syringe filter) is added to the vial.

50 mM MPAA (42.1 g, 0.26 mmol) (MPAA: 4-mercaptphenyl acetic acid (Sigma-Aldrich, Cat. #:653152))

20 mM TCEP (replaceable by HCl) (28.7 g, 0.1 mmol) (TCEP: tris(2-carboxyethyl)phosphine hydrochloride (Sigma-Aldrich, Cat. #:C4706))

(3) pH Adjustment of NCL Buffer

A pH value of the NCL buffer prepared in section (2) is adjusted at 7.1 by 2M NaOH or 1M HCl.

[Reaction of Binding Substance with Temperature Responsive Polyamino Acid]

A reaction of a binding substance with a temperature responsive substance is performed by the following procedure.

(1) The peptide (e.g., polyamino acid)-thioester and the Cys-peptide (e.g., Protein A) are accurately measured and put in a tube. Here, the addition of a thiol to the C-terminal of the polyamino acid and the addition of Cys to the N-terminal of the binding substance will be described later. Here, if the peptide has a molecular mass of 1500 Da or less, 3 mM of the peptide has an about 5 mg weight.

(2) The NCL buffer is added to the tube containing the peptide-thioester and the Cys-peptide, thereby to rapidly dissolve the peptides. The pH value of the solution dissolving the peptides is measured, and set at 7.0 where necessary. When pH adjustment is needed, it is preferable to use a low concentrated NaOH solution (e.g., 0.2 M) for adjusting the pH value. Here, if the pH value is more than 7.0, the peptides are to be hydrolyzed (3) The reaction is monitored by liquid chromatography mass spectrometry (LCMS) or matrix assisted laser desorption/ionization—time of flight mass spectrometry (MALDI-TOF MS). After the NCL buffer is added to the peptides, the reaction is monitored at the time points of 0 min, 30 min, 1 hr, 2 hr, 4 hr, 8 hr and 16 hr. Generally, the reaction occurs during 1-16 hr. At each time point, 10 μm of the reaction solution is taken in a microtube, and diluted by 20 fold via adding 190 μm of $AcCN:H_2O$ (0.08%:0.1% TFA v/v)=1:1 solution so as to quench the reaction (e.g., to securely quench the reaction, the pH value has to be lowered to 4 by 1M HCl).

(4) Just after the completion of the reaction, the resulting solution is diluted with 1M GuHCl (using 0.1% TFA (solvent A)), via lowering the pH value thereby to quench the reaction.

<Method for Adding Cysteine to N-Terminal of Binding Substance>

When the N-terminal of the binding substance is not cysteine, cysteine may be added to the N-terminal of the binding substance by the following procedure.

DNA encoding the gene of the target protein (i.e., binding substance) is inserted into the multi cloning site of the pTYB21 vector (e.g., SalI-PstI). The inserted pTYB21 vector is introduced in *E. Coli* Strain ER2566. Cultivation of the *E. Coli* produces the target protein fused with a tag consisting of intein and chitin-binding domain (CBD) at the N-terminal. The produced target protein is attached to chitin beads. Then, a thiol reagent (DTT: dithiothreitol or 2-mercaptethansulfonic acid) is used to cleave the target protein (i.e., binding substance) having cysteine added at the N-terminal from the beads. Hereby, the protein having cysteine added at N-terminal (i.e., binding substance) is collected.

<Method for Adding Thiol to C-Terminal of Polyamino Acid>

DNA encoding the polyamino acid sequence is inserted to the multi cloning site of the pTXB1 vector (e.g., NdeI-SalI or SpeI). The inserted pTXB1 vector is introduced into *E. Coli* Strain ER2566. Cultivation of the *E. Coli* produces a polyamino acid fused with a tag consisting of intein and chitin binding domain (CBD) at the C-terminal. The produced polyamino acid is attached to the chitin beads. Then, a thiol reagent (i.e., DTT or 2-mercaptethansulfonic acid) is used to cleave the polyamino acid having a thioester at the C-terminal from the beads. Hereby, the polyamino acid having thioester at C-terminal is collected.

<Fixing of Temperature Responsive Polyamino Acid to Carrier>

The temperature responsive polyamino acid may be fixed to a carrier by the same operation as for other ligand proteins. Here, an example of fixing to a carrier will be described. However, other fixing methods may be operable.

[Fixing Method onto HiTRAP NHS-Activated HP Column (1 ml)]

(1) Preparation of Column

A syringe is carefully connected to a column so that no babbles are introduced in the column. Then, 1 mM HCl (5 ml) is fed at the flow rate of 1 drop/sec (or 0.2-1 ml/min).

(2) Coupling Reaction

A solution (1 ml) containing the ligand protein (or temperature responsive polyamino acid) is fed in the column at the flow rate of 1 drop/sec (or 0.2-1 ml/min), and the outlet of the column is sealed by a stop plug. The column is left at room temperature for 15-30 min or at 4° C. for 4 hr. Then, the coupling buffer (3 ml) is fed in the column at the flow rate of 1 drop/sec (or 0.2-1 ml/min). Here, it is described that 100 mM sodium hydrogen carbonate with pH 8.3 is used as a coupling buffer but instead 500 mM sodium chloride may be also used as a coupling buffer.

(3) Blocking of Unreacted Active Group

After completion of feeding the coupling buffer, a blocking buffer (6 ml) is fed in the column at the flow rate of 1 drop/sec (or 1-2 ml/min). Then, a cleaning buffer (6 ml) is fed in the column at the flow rate of 1 drop/sec (or 1-2 ml/min). After that, a blocking buffer (6 ml) is fed in the column at the flow rate of 1 drop/sec (or 1-2 ml/min). The resulting column is left at room temperature for 15-30 min or at 4° C. for 4 hr. Here, it is described that 500 mM monoethanol amine with pH 8.3 is used as a blocking buffer but instead 500 mM sodium chloride may be also used as a blocking buffer. Further, it is described that 100 mM sodium acetate with pH 4.0 is used as a cleaning buffer but instead 500 mM sodium chloride may be also used as a cleaning buffer.

(4) Cleaning and Equilibration of Column

The cleaning buffer (6 ml) is fed in the column at the flow rate of 1 drop/sec (or 1-2 ml/min). Then, the blocking buffer (6 ml) is fed in the column at the flow rate of 1 drop/sec (or 1-2 ml/min). Further, the cleaning buffer (6 ml) is fed in the column at the flow rate of 1 drop/sec (or 1-2 ml/min). After that, an equilibration buffer (6 ml) is fed in the column at the flow rate of 1 drop/sec (or 1-2 ml/min), thereby to completely prepare the ligand fixed column (i.e., temperature responsive polyamino acid fixed column (or temperature responsive specific adsorption/desorption column). Note that 0.1 M phosphate buffer with pH7.4 may be used as an equilibration buffer.

Meanwhile, another method for improving an absorption amount per unit volume of the carrier may be available other than the method as mentioned above. That method may be performed via uniforming an orientation of a ligand (i.e., temperature responsive polyamino acid) on the carrier. For example, a peptide specifically bonding to a specific portion of a protein is prepared. The resulting peptide allows the orientation of the protein to be uniformed in the direction of the binding easily formed between the protein and the peptide. This procedure results in improvement of the absorption amount per unit volume of the carrier.

<Purification Method Using Temperature Responsive Specific Adsorption/Desorption Column>

Next, an example of a purification method using a temperature responsive specific adsorption/desorption column will be described.

A recovered culture solution of which temperature is kept at 20° C. or less is passed through the temperature responsive specific adsorption/desorption column prepared as mentioned above (i.e., column containing a carrier, a temperature responsive polyamino acid bonded to the carrier, and a binding substance bonded to the temperature responsive polyamino acid and specifically bonding to a target substance). Hereby, an antibody protein which is a target substance is made adsorbed by the column. After that, a buffer heated at 37° C. (20 mM phosphate, pH7.0) is passed through the column, thereby eluting the antibody protein.

Figure 7A:
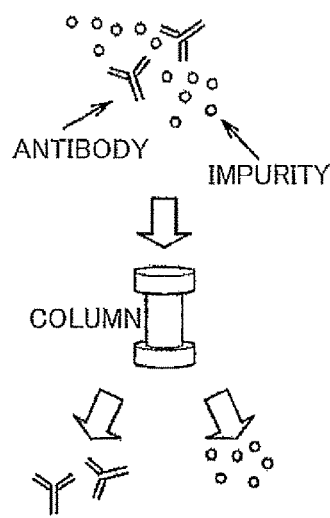
FIGS. 7A and 7B show a difference in purification methods between a temperature responsive column and a conventional column.
Figure 7B:
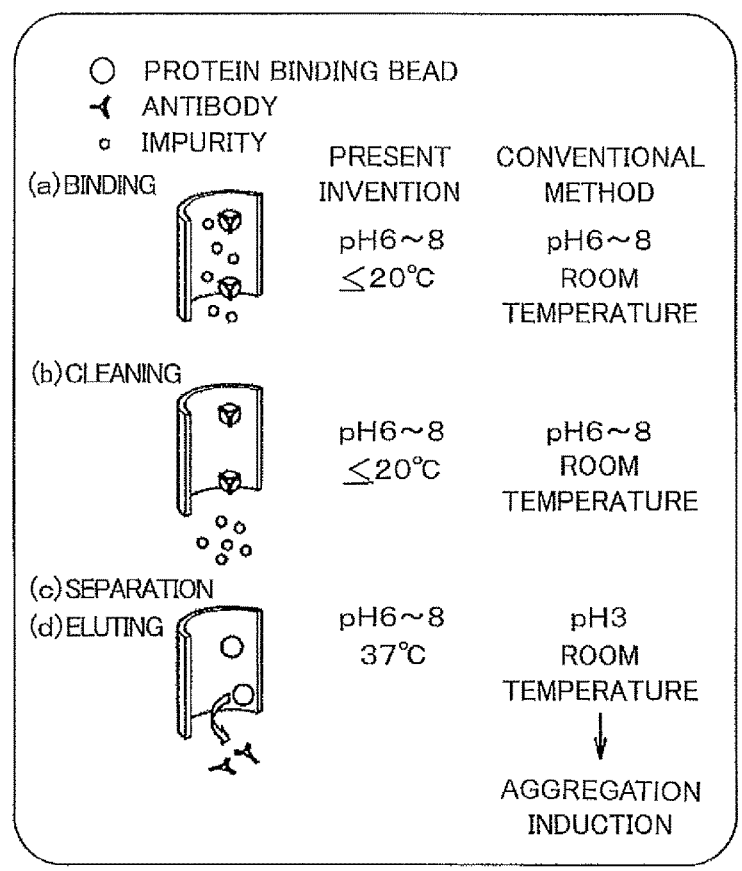

FIGS. 7A-7B show a difference between the temperature responsive specific adsorption/desorption column and a conventional Protein A column (i.e., column containing Protein A bonded to carrier). The purification method includes a binding step ((a) of FIG. 7B), a cleaning step ((b) of FIG. 7B), and a separation/eluting step ((c) and (d) of FIG. 7B).

First, a culture solution containing the antibody and impurities is passed through the column. When the column is packed with Protein A bonded beads, the antibody is to be bonded to the beads, while the impurities are not bonded to the beads. Then, cleaning of the column removes the impurities. In the purification/eluting step, the antibody is to be separated from the Protein A bonded beads by reducing the binding strength between the antibody and the Protein A bonded beads.

As shown in FIGS. 7A-7B, in the conventional method, the binding step and cleaning step are performed under the conditions of a neutral pH value and room temperature, and the separation/eluting step is performed under the conditions of a low pH value and room temperature. The conventional method allows the binding strength between the antibody and the Protein A bonded beads to be weaken, thereby eluting the antibody. However, when the antibody is exposed to the low pH condition, the antibody is to be bonded each other, leading to formation of aggregations (i.e., aggregation induction). This aggregation of antibody is not preferable due to the decrease in the yield of the good-quality antibody.

On the contrary, as shown in FIGS. 7A-7B, in the purification device of the present invention (i.e., in Present Invention of FIG. 7B, the binding step and cleaning step are performed in a low temperature such as 20° C. or less, and the purification/eluting step is performed at an elevated temperature such as 37° C. This procedure makes the binding strength changed so as to elute the antibody. In other words, in the purification device of the present invention, all of the steps are performed at a neutral pH value, and the temperatures are changed in the range without denaturing the antibody. Accordingly, the purification device of the present invention enables the antibody to be obtained without causing the aggregation thereof. Further, the purification device of the present invention enables the yield of the good-quality antibody to be increased.

EXAMPLE

Hereinafter, the present invention will be described in more detail referring to examples. However, the present invention is not limited to those examples.

<Construction of Temperature Controllable Protein A Material>

(1) Preparation of Temperature Responsive Polylysine

Temperature responsive polylysine was prepared by the following procedure. 1-Ethyl-3-(3-dimethylaminopropyl) carbodiimide (WSC) (290 mg), N-hydroxy-succinimide (NHS) (170 mg) and valeric acid (130 mg) were dissolved in pure water (4 ml). The resulting solution was cooled at 4° C., and ε-polylysine (140 mg, mixture of different molecular weights) was added in the solution under stirring condition. After stirring at ambient temperature for 2 hr, unreacted low molecular weight compounds were removed by a dialysis membrane under stirring condition for 24 hr. Use of different types of dialysis membrane gave three types of temperature responsive polylysine: a temperature responsive polylysine with mw of 3.5 kDa or more, a temperature responsive polylysine with mw of 10 kDa or more and a temperature responsive polylysine with mw of 20 kDa or more.

(2) Attachment of Temperature Responsive Polylysine to Matrix

Figure 8:
FIG. 8 shows a resin plate of which surface is treated with an amino group.

The well surfaces of the resin plate were subjected to the amino group addition treatment (in FIG. 8). The prepared three types of temperature responsive polylysine were respectively made covalently bonded onto the well surfaces by the following procedure. Here, the addition of the amino group to the well surfaces of the resin plate was performed by a conventional method. Next, glutaraldehyde was diluted with a carbonate buffer to contain a 2% glutaraldehyde in the solution. The carbonate buffer containing 2% glutaraldehyde (150 μm) was added into each well, and the reaction was carried out at 37° C. for 2 hr. After each well was washed by pure water three times, the temperature responsive polylysine (100 μm) was added to each well, and the reaction was carried out for 2 hr. After that, each well was washed by the PBS (phosphate buffer) three times.

Note that the conventional method described above was carried out as the following procedure. The procedure was carried out by the steps of treating a polystyrene plate produced via injection molding with high-frequency low temperature plasma as making an oxygen gas under a reduced pressure flow for 3 hr, immersing the plate in 10% γ-aminopropyltrimethoxysilane methanol solution to perform an aminosilane treatment via being left for 16 hr, washing the plate by distilled water, and drying the plate to form the amino group bonded on the well surfaces of the plate.

(3) Bonding of Protein a to Temperature Responsive Polylysine

The 2% glutaraldehyde solution was added to the resin plate having the well surfaces to which the temperature responsive polylysine was covalently bonded as prepared in Section (2), and the reaction was carried out for 2 hr. After the wells were washed by pure water, 100 μl of Protein A (10 μg/ml) was added to each well, and the reaction was carried out for 2 hr. After that, each well was washed by the PBS (phosphate buffer) three times.

<Adsorption/Desorption Evaluation of Antibody (IgG) to/from Temperature Controllable Protein A Material Via Temperature Controlling>

Adsorption/desorption performance of the temperature controllable Protein A thus prepared as above was evaluated by controlling temperatures as the following procedure.

The well surfaces of the resin plates were subjected to the blocking treatment with 5% skim milk so that proteins other than the Protein A were not nonspecifically adsorbed onto the surfaces. After each well was washed by the cleaning buffer (200 μl) three times, streptavidin-peroxydase conjugate (50 μl) was added to each well, and the resulting mixture was incubated at 4° C. overnight.

For evaluating the effect of the temperature responsibility, one group of the resin plates was treated under 37° C. condition, while the other group of the resin plates was treated under 4° C. condition. In both groups, after each well was washed by the cleaning buffer (200 μm) three times, 50 μl of TMB (3,3',5,5'-tetramethylbenzidine) acting as a chromophoric substance was added to each well so as to carry out the coloring reaction. Then, absorbances at λ 650 nm were measured in both groups.

Figure 9:
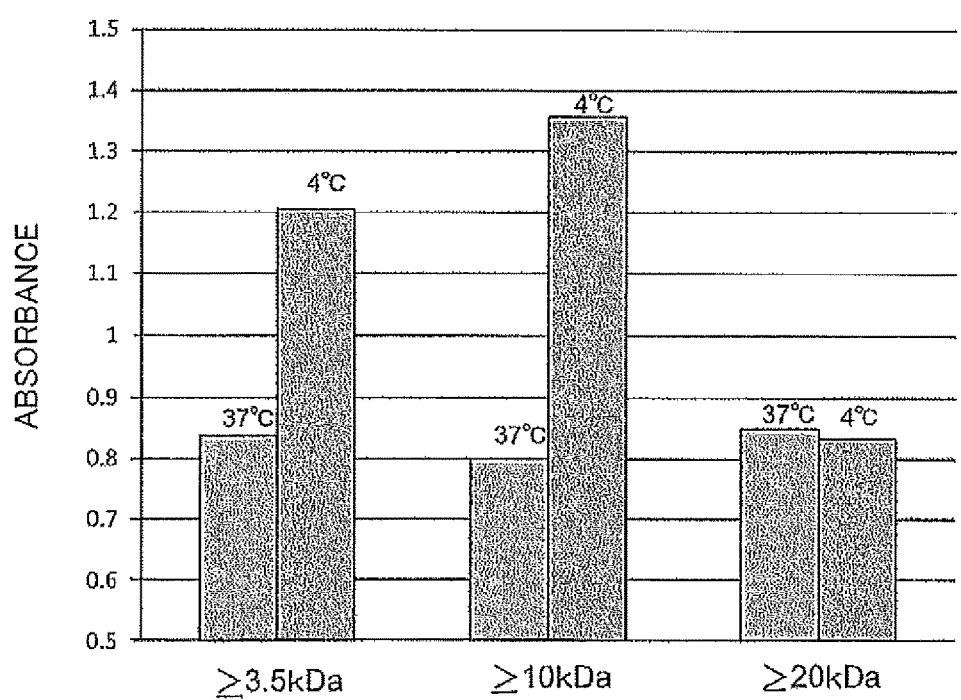
FIG. 9 shows results of adsorption/desorption evaluation conducted by temperature controlling.

FIG. 9 shows the measurement results of the absorbances. The results indicate that the absorbances of the 4° C. condition group are higher than the absorbances of the 37° C. condition group when the tested polylysines respectively have the molecular weights of 3.5 kDa or more and 20 kDa or more (i.e., bonding at 4° C. and separating at 37° C.). This indicates that the binding strength of the Protein A to the antibody (IgG) is higher under 4° C. condition. Further, this indicates that the binding strength thereof is particularly high when the polylysin has a molecular weight of 10 kDa or more.

In contrast, when the polylysine has a molecular weight of 20 kDa or more, there is no difference in the absorbances between the 4° C. condition group and the 37° C. condition group. This indicates that the binding strength does not change by the temperature controlling

REFERENCE SIGNS

1 Medium Reservoir
2 Affinity Column
3 Anion Exchange Column
4 Cation Exchange Column
5 Ultrafiltration (UF) Apparatus
6 Eluent Tank
7 Cooling Apparatus
8 Disinfection Filter
9 Fraction Tank
10 Reservoir

What is claimed is:

1. A purification device for purifying a target substance, comprising a column and a filler packed in the column, wherein
the filler comprises a carrier, a temperature responsive polyamino acid bonded to the carrier, and a binding substance bonded to the temperature responsive polyamino acid, which binding substance has been adapted for specifically bonding to the target substance to be purified,
wherein the binding substance is a protein having a cysteine (Cys) on the N-terminal thereof that binds to a thiol group on the C-terminal of the polyamino acid, and the polyamino acid includes in side chains at least one of an amphipathic group, a hydrophobic group and a hydrophilic group.

2. The purification device as described in claim 1, wherein the temperature responsive polyamino acid changes a structure between a conformation in which the target substance is bounded to the binding substance and a conformation in which the target substance thus bonded to the binding substance is separated therefrom, and the structural change occurs in the range from 0° C. to 60° C.

3. The purification device as described in claim 1, wherein the temperature responsive polyamino acid is at least a member selected from a group of polylysine, polyglutamic acid and polyasparagine.

4. The purification device as described in claim 1, wherein the binding substance is Protein A and the target substance is an antibody.

5. The purification device as described in claim 1, further comprising a temperature controller which is configured to change a temperature of the temperature responsive polyamino acid in the range from 0° C. to 60° C.

6. The purification device as described in claim 1, wherein the temperature responsive polyamino acid includes a carboxyl butylamino group or a carboxyl propylamino group in the side chains.

7. The purification device as described in claim 1, wherein the temperature responsive polyamino acid includes both a dodecylamino group and a hydroxy alkylamino group in the side chains.

8. The purification device as described in claim 7, wherein the temperature responsive polyamino acid is a polyasparagine.

9. The purification device as described in claim 1, wherein the temperature responsive polyamino acid includes a hydroxy alkylamino group in the side chains.

10. The purification device as described in claim 9, wherein the temperature responsive polyamino acid is a polyglutamic acid.

11. A purification method for purifying a target substance, the method comprising:
- a binding step of passing a solution containing a target substance and impurities through a column packed with a filler comprising a carrier, a temperature responsive polyamino acid bonded to the carrier and a binding substance bonded to the temperature responsive polyamino acid, which binding substance has been adapted for specifically bonding to the target substance to be purified, thereby making the target substance bond to the binding substance;
- a cleaning step of cleaning an inside of the column via washing out the impurities without separating the target substance thus bonded to the binding substance;
- a separation step of separating the target substance bonded to the binding substance via changing a temperature of the temperature responsive polyamino acid after the inside of the column is cleaned; and
- an eluting step of eluting the separated target substance from the column,
- wherein the binding substance is a protein having a cysteine (Cys) on the N-terminal thereof that binds to a thiol group on the C-terminal of the polyamino acid, and the polyamino acid includes in side chains at least one of an amphipathic group, a hydrophobic group and a hydrophilic group.

12. The purification method as described in claim 11, wherein
the temperature responsive polyamino acid changes a structure between a conformation in which the target substance is bonded to the binding substance and a conformation in which the target substance thus bonded to the binding substance is separated therefrom; and the structural change occurs in the range from 0° C. to 60° C.

13. The purification method as described in claim 11, wherein the temperature responsive polyamino acid is at least a member selected from a group of polylysine, polyglutamic acid and polyasparagine.

14. The purification method as described in claim 11, wherein the binding substance is Protein A and the target substance is an antibody.

15. The purification method as described in claim 11, wherein the separation step is performed in the range from 0° C. to 60° C.

16. The purification method as described in claim 11, wherein the eluting step is performed at pH values from 5 to 9.

17. The purification method as described in claim 11, wherein the temperature responsive polyamino acid includes a carboxyl butylamino group or a carboxyl propylamino group in the side chains.

18. The purification method as described in claim 11, wherein the temperature responsive polyamino acid includes both a dodecylamino group and a hydroxy alkylamino group in the side chains.

19. The purification method as described in claim 18, wherein the temperature responsive polyamino acid is a polyasparagine.

20. The purification method as described in claim 11, wherein the temperature responsive polyamino acid includes a hydroxy alkylamino group in the side chains.

21. The purification method as described in claim 11, wherein the temperature responsive polyamino acid is a polyglutamic acid.

* * * * *